United States Patent
Yokoyama et al.

(10) Patent No.: US 9,326,692 B2
(45) Date of Patent: May 3, 2016

(54) BLOOD PRESSURE MEASUREMENT DEVICE AND BLOOD PRESSURE MEASUREMENT METHOD

(75) Inventors: Toshihiko Yokoyama, Nagano (JP); Kuniaki Tanaka, Nagano (JP); Toshinobu Sakurai, Samukawa-machi (JP)

(73) Assignee: Seiko Epson Corporation, Tokyo (JP)

( * ) Notice: Subject to any disclaimer, the term of this patent is extended or adjusted under 35 U.S.C. 154(b) by 356 days.

(21) Appl. No.: 12/947,185

(22) Filed: Nov. 16, 2010

(65) Prior Publication Data

US 2011/0118613 A1    May 19, 2011

(30) Foreign Application Priority Data

Nov. 17, 2009  (JP) ................. 2009-261583

(51) Int. Cl.
*A61B 5/0215*  (2006.01)
*A61B 5/022*  (2006.01)

(52) U.S. Cl.
CPC .......... *A61B 5/022* (2013.01); *A61B 2560/0223* (2013.01); *A61B 2560/0257* (2013.01)

(58) Field of Classification Search
CPC ........... A61B 5/022; A61B 2560/0257; A61B 2560/0223
USPC ................. 600/481, 485, 488, 507
See application file for complete search history.

(56) References Cited

U.S. PATENT DOCUMENTS

| | | | | | |
|---|---|---|---|---|---|
| 4,625,277 | A | * | 11/1986 | Pearce et al. | 600/493 |
| 4,779,461 | A | * | 10/1988 | Gilman et al. | 73/865.3 |
| 4,779,626 | A | * | 10/1988 | Peel et al. | 600/488 |
| 5,103,832 | A | * | 4/1992 | Jackson | 600/488 |
| 5,778,879 | A | * | 7/1998 | Ota et al. | 600/485 |
| 5,957,853 | A | * | 9/1999 | Giuffre | 600/486 |
| 6,241,684 | B1 | * | 6/2001 | Amano et al. | 600/531 |
| 6,872,182 | B2 | * | 3/2005 | Kato et al. | 600/490 |
| 2008/0306354 | A1 | * | 12/2008 | Mason | 600/301 |

FOREIGN PATENT DOCUMENTS

| | | |
|---|---|---|
| JP | 62-66836 A | 3/1987 |
| JP | 02-55033 A | 2/1990 |
| JP | 2007-054648 A | 3/2007 |
| JP | 2009-189485 A | 8/2009 |
| WO | WO-02/39893 A1 | 5/2002 |

* cited by examiner

*Primary Examiner* — Patricia Mallari
*Assistant Examiner* — Michael Catina
(74) *Attorney, Agent, or Firm* — Global IP Counselors, LLP

(57) ABSTRACT

A blood pressure measurement device is characterized in that the said device is designated to arithmetically apply to the computed blood pressure value a correction value that is in accordance with the difference in atmospheric pressure between the position of the blood pressure transmitting part and the position of the heart of the subject wearing the blood pressure transmitting part as obtained from the sensor signal, on the basis of the internal pressure variation of the blood pressure transmitting part.

7 Claims, 5 Drawing Sheets

BLOOD PRESSURE MEASUREMENT DEVICE AND BLOOD PRESSURE MEASUREMENT METHOD

BACKGROUND

1. Technological Field

The present invention relates to a blood pressure measurement device and blood pressure measurement method.

2. Background Technology

Medical insurance in Japan applied insurance points to 24-hour blood pressure gauges for the first time due to a change to insurance medical fee points in 2008. This came about as a result of medical and administrative recognition that a correct diagnosis of high blood pressure cannot be made based on a single blood pressure measurement from a specific time. Such a recognition is a breakthrough in understanding high blood pressure, and indicates a need for a new generation in blood pressure management that goes beyond conventional blood pressure management.

Specifically, blood pressure values vary continually, and by precisely comprehending this variation to achieve a level of blood pressure management not heretofore possible by the conventional technique, it may become possible to reduce the current incidence of circulatory system diseases, increase the QOL of individuals in the future aging society, bring down total health care cost for the entire country, and avert medical financial bankruptcy.

The two methods described below are now commonly used for noninvasive measurement of blood pressure. The first method is known as auscultation. After applying a pressure equal to or greater than the systolic blood pressure value from outside an artery, the pressure is gradually relieved, whereupon the blood vessel audibly pulsates in a specific pressure range and emits a so-called Korotkoff sound. Auscultation is a method in which the pressure value when the Korotkoff sound begins to occur at the abovementioned relieving of pressure is determined as the systolic blood pressure, and the pressure value when the sound disappears is determined as the diastolic blood pressure.

The second method is known as the oscillometric method. When pressure is applied from the outside in the same manner as in the auscultation method, since the mechanical characteristics of the arterial wall are nonlinear, the volume of the blood vessel varies with each heartbeat, and the pulse wave amplitude varies in nonlinear fashion. After a pressure equal to or greater than the systolic blood pressure is applied in the same manner as in the auscultation method, the pressure is gradually relieved, whereupon the blood vessel begins to pulsate when the pressure applied is below the systolic blood pressure, and after the maximum volume variation occurs at the average blood pressure, the pulse wave pulsation again disappears at or below the diastolic blood pressure. By thus simultaneously recording the pressure value as well as the volume variation of the blood vessel at the time the pressure value occurs, the systolic blood pressure, the average blood pressure, and the diastolic blood pressure can be determined. The oscillometric method is widely used by particularly in blood pressure gauges worn on the wrist, since a pulse waveform is relatively easy to express as an electrical signal.

The medical definition of blood pressure is the intravascular pressure in the aortic root, and another blood pressure value measured noninvasively is thus an estimate of the true blood pressure. Since blood also naturally has weight, measurement of blood pressure by the auscultation method or the oscillometric method must take place at the same height as the heart. In a common blood pressure gauge, in the case of measurement at the upper arm, for example, the cuff must be worn at the same height as the heart, and for measurement at the wrist, the wrist must be raised to the height of the heart. Otherwise, a correction must be made in accordance with the difference in height with respect to the heart (so-called water head correction). Since the correction for height corresponds to 10 mmHg for a water head of 13.6 cm, for example, a correction of approximately 7.35 mmHg must be made for every 10 cm.

A blood pressure measurement device has been disclosed in which angle detection means is provided for the upper arm in addition to a forearm angle detection means, and the height of a cuff and the heart are detected based on the detected angles of the forearm and upper arm (see Patent Document 1, for example).

In another blood pressure measurement device (see Patent Document 2, for example), an angle sensor is also provided to the cuff, and the angle formed by an air bag is detected. A straight line connecting the artery and the angle sensor when the angle sensor in the substantial center of the air bag is directly over the artery is used as a reference, and a determination is made based on a signal from the angle sensor during wearing of the cuff as to whether the angle of the straight line connecting the artery and the angle sensor from the abovementioned reference is less than a threshold value. This determination is made prior to blood pressure measurement and displayed. A user can therefore observe the display to achieve the proper fit of the cuff prior to measurement, and then perform a measurement.

In another disclosed blood pressure measurement device (see Patent Document 3, for example), by more accurately determining the positions of the cuff and the heart, blood pressure is measured without the measurement being affected by the subject's posture during measurement and fluctuation in physical characteristics of the subject. In this technique, the height of the cuff and heart is detected based on inputted values for the subject's upper arm length and forearm length, and detected angles for the pitch direction and roll direction of the forearm. Angle detection means for the upper arm is provided in addition to forearm angle detection means, and the height of the cuff and heart is detected based on the detected angles of the forearm and upper arm. Angles in the pitch direction and roll direction of the forearm are also detected by two-axis angle detection means, and the height of the cuff and heart is detected based on these detection values.

A blood pressure measurement device has also been disclosed (see Patent Document 4, for example) in which the body of the blood pressure measurement device worn by the subject is configured so as to be capable of integrally connecting with a processor, and the blood pressure measurement operation is automatically performed based on a mode inputted from the processor side.

In another disclosed blood pressure measurement device (see Patent Document 5, for example), a blood pressure measurement time or medication time is announced by a notification unit, and measurement can be reliably performed without being forgotten even when the device is used at home, and the measurement results are displayed by display means. Since the measurement results and measurement time are stored in a convenient memory for portability, a blood pressure trend diagram or other summary can be displayed by connecting an interface to a host computer during a hospital visit.

PRIOR ART REFERENCES

Patent Documents

[Patent Document 1] Japanese Laid-open Patent Publication No. 2007-54648

[Patent Document 2] Japanese Laid-open Patent Publication No. 2009-189485
[Patent Document 3] WO 2002/039893
[Patent Document 4] Japanese Laid-open Patent Publication No. 2-55033
[Patent Document 5] Japanese Laid-open Patent Publication No. 62-66836

DISCLOSURE OF THE INVENTION

Problems to Be Solved by the Invention

Particularly in the case of a wrist blood pressure gauge, the position of the wrist varies freely, and the subject is therefore informed in the explanatory documentation or the like that measurement must be performed at the height of the heart. However, the wrist is not necessarily in the optimum position, and measurement error may therefore occur.

Conventional techniques for avoiding this problem include a technique of using a sensor to detect the tilt of the arm with respect to the horizontal, for example, indirectly detecting that the arm is at the same height as the heart, and performing measurement only when the arm is in the optimum position.

However, the optimum value is not necessarily detectable in all orientations, and adding all of the devices described above also increases the size of the overall product, and the unit cost of the product also increases.

A 24-hour blood pressure gauge used to correctly diagnose high blood pressure automatically measures blood pressure every 30 minutes regardless of activity or sleep states. In order for a 24-hour blood pressure gauge to function on the wrist, the wrist must always be raised to the position of the heart at the time of measurement during daily activities, and this posture must be maintained for a certain period of time, thus inconveniencing the subject. Since measurement error also increases, devices which are used only on the upper arm have been used in the past. A method for avoiding the problems described above may involve extending a tube to a point on the arm that corresponds to the position of the heart, and using the pressure value at that point to correct the measurement value, but because of the resultant complex configuration of the device, such a method has not yet been implemented.

There is a need for a blood pressure gauge which can be worn continuously and is capable of frequent measurement, rather than measuring blood pressure at a specific location once in a day, such as in the case of the conventional blood pressure gauge.

SUMMARY

Means Used to Solve the Above-Mentioned Problems

The present invention was developed in order to overcome at least some of the problems described above, and the present invention can be realized in the form of the embodiments or application examples described below.

Application Example 1

The blood pressure measurement device of the present application example is a blood pressure measurement device characterized in comprising a sensor for measuring air pressure; a measurement switching unit for switching between measurement of an internal pressure variation of a blood pressure transmitting part by the sensor, and measurement of atmospheric pressure at the position of the blood pressure transmitting part and the position of the heart of a subject wearing the blood pressure transmitting part by the sensor; a blood pressure measuring part for acquiring a sensor signal of the sensor from the measurement of the internal pressure variation of the blood pressure transmitting part by the sensor, and computing a blood pressure value on the basis of the internal pressure variation of the blood pressure transmitting part, obtained from the sensor signal; and a blood pressure value correction unit for acquiring the sensor signal of the sensor for measuring the atmospheric pressure at the position of the blood pressure transmitting part and the position of the heart of the subject wearing the blood pressure transmitting part, and arithmetically applying to the computed blood pressure value a correction value that is in accordance with the difference in atmospheric pressure between the position of the blood pressure transmitting part obtained from the sensor signal and the position of the heart of the subject wearing the blood pressure transmitting part, on the basis of the internal pressure variation of the blood pressure transmitting part.

Water head correction is thereby simultaneously applied to the obtained blood pressure value by switching the sensor as needed to a precision suitable for each measurement. Water head correction can therefore be realized using minimal additional circuitry, and blood pressure can be reliably measured without inconvenience for the subject.

Since the degree of height precision depends on the sensor, measurement must be repeated a certain number of times or more with some sensors, and because a certain amount of time or longer is required for each measurement, the necessary sampling frequency for obtaining an oscillometric waveform for blood pressure measurement is sometimes not achieved. In such cases, by providing modes whereby sampling can be performed by a high-precision, low-speed mode in the case of measuring the altitude of the heart, and sampling can occur at high speed at the necessary precision in the case of obtaining an oscillometric waveform, and switching between modes as needed, the number of required sensors can be prevented from increasing, and unnecessary increases in cost and installation size can be minimized.

Application Example 2

The blood pressure measurement device of the present application example is the blood pressure measurement device described above, characterized in that the sensor signal is sampled by a method in which measuring the internal pressure variation of the blood pressure transmitting part through the use of the sensor is faster than measuring the atmospheric pressure at the position of the blood pressure transmitting part and the position of the heart of the subject wearing the blood pressure transmitting part through the use of the sensor, and measuring the atmospheric pressure at the position of the blood pressure transmitting part and the position of the heart of the subject wearing the blood pressure transmitting part through the use of the sensor is more precise than measuring the internal pressure variation of the blood pressure transmitting part through the use of the sensor.

Water head correction can thereby be simultaneously applied to the obtained blood pressure value by switching the sensor as needed to a precision suitable for each of blood pressure measurement and altitude measurement.

Application Example 3

The blood pressure measurement method is characterized in comprising acquiring a sensor signal of a sensor for measuring air pressure, from a measurement of the internal pressure variation of the blood pressure transmitting part by the sensor, and computing a blood pressure value on the basis of the internal pressure variation of the blood pressure transmitting part, obtained from the sensor signal; switching between measurement of the internal pressure variation of the blood pressure transmitting part by the sensor, and measurement of atmospheric pressure at the position of the blood pressure transmitting part and the position of the heart of the subject wearing the blood pressure transmitting part by the sensor; and acquiring the sensor signal of the sensor for measuring the atmospheric pressure at the position of the blood pressure transmitting part and the position of the heart of the subject wearing the blood pressure transmitting part, and arithmetically applying to the computed blood pressure value a correction value that is in accordance with the difference in atmospheric pressure between the position of the blood pressure transmitting part and the position of the heart of the subject wearing the blood pressure transmitting part as obtained from the sensor signal, on the basis of the internal pressure variation of the blood pressure transmitting part.

Water head correction is thereby simultaneously applied to the obtained blood pressure value by switching the sensor as needed to a precision suitable for each measurement. Water head correction can therefore be realized using minimal additional circuitry, and blood pressure can be reliably measured without inconvenience for the subject.

Since the degree of height precision depends on the sensor, measurement must be repeated a certain number of times or more with some sensors, and because a certain amount of time or longer is required for each measurement, the necessary sampling frequency for obtaining an oscillometric waveform for blood pressure measurement is sometimes not achieved. In such cases, by providing modes whereby sampling can be performed by a high-precision, low-speed mode in the case of measuring the altitude of the heart, and sampling can occur at high speed at the necessary precision in the case of obtaining an oscillometric waveform, and switching between modes as needed, the number of required sensors can be prevented from increasing, and unnecessary increases in cost and installation size can be minimized.

Application Example 4

The blood pressure measurement method of the present application example is the blood pressure measurement method described above, characterized in that the sensor signal is sampled by a method in which measuring the internal pressure variation of the blood pressure transmitting part through the use of the sensor is faster than measuring the atmospheric pressure at the position of the blood pressure transmitting part and the position of the heart of the subject wearing the blood pressure transmitting part through the use of the sensor, and measuring the atmospheric pressure at the position of the blood pressure transmitting part and the position of the heart of the subject wearing the blood pressure transmitting part through the use of the sensor is more precise than measuring the internal pressure variation of the blood pressure transmitting part through the use of the sensor.

Water head correction can thereby be simultaneously applied to the obtained blood pressure value by switching the sensor as needed to a precision suitable for each of blood pressure measurement and altitude measurement.

DETAILED DESCRIPTION OF EXEMPLARY EMBODIMENTS

Figure 1:
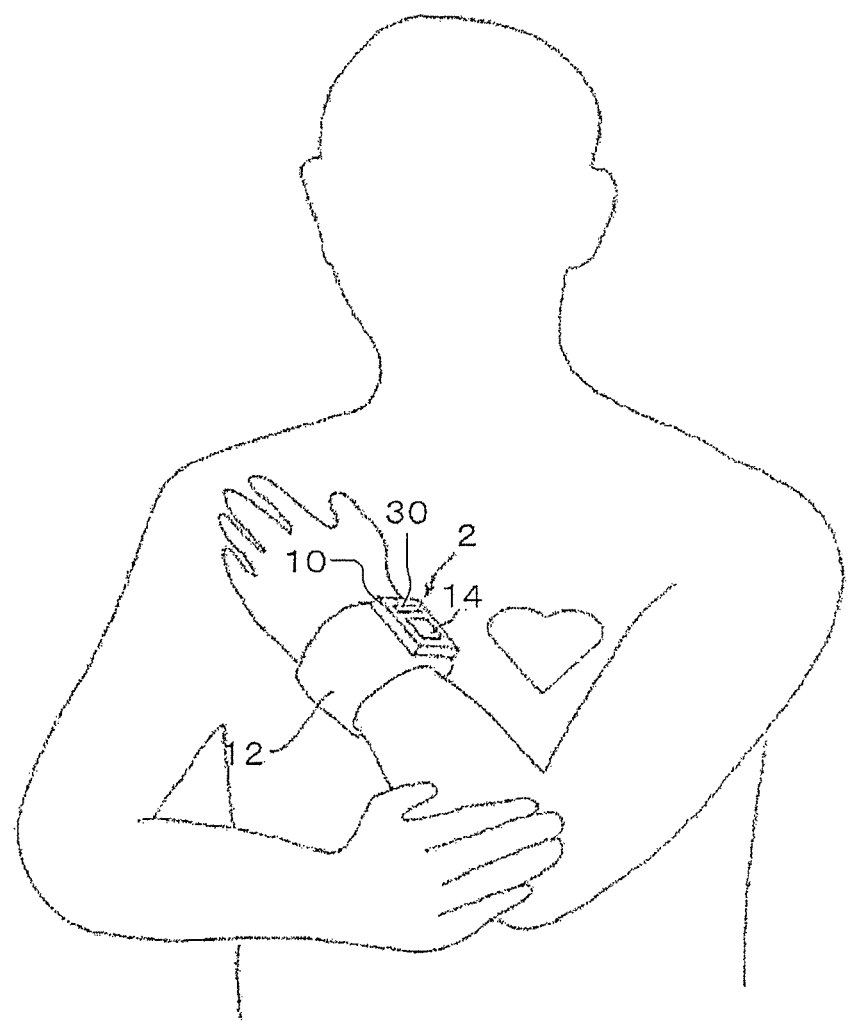
FIG. 1 is a view showing the posture for measurement using the electronic blood pressure gauge according to the present embodiment.

FIG. 1 is a view showing the posture for measurement using the electronic blood pressure gauge according to the present embodiment.

The blood pressure measurement device 2 according to the present embodiment uses a pressure sensor provided to a body 10 of the blood pressure measurement device 2 worn on the wrist to compute the measurement posture of a subject, i.e., the height difference between the heart and the pressure-based position of the blood pressure measurement device 2, and determine the measurement posture or correct the blood pressure value. In the blood pressure measurement device 2 according to the present embodiment, it is recommended that measurement be performed in a posture in which the armpit is closed and the forearm is placed against the chest, as shown in FIG. 1 (at this time, the other hand is preferably used as a support so that the elbow of the arm on which the blood pressure measurement device 2 is worn does not move away from the body). The body 10 is also attached so as to be positioned on the side of the thumb with respect to a belt-shaped cuff (blood pressure transmitting part) 12 wrapped around the wrist. Consequently, when the measurement posture shown in FIG. 1 is assumed, a display unit 14 faces upward, and the subject can easily monitor the display. An operation input unit 30 which includes a pressure key and other keys can also be easily operated by the subject in the same manner.

Figure 2:
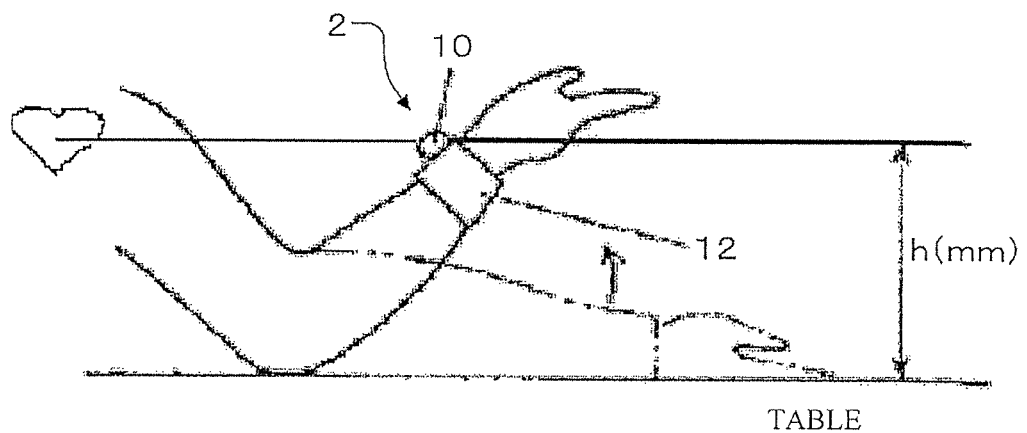
FIG. 2 is a view showing the relationship between the position of the cuff and the height of the heart.

FIG. 2 is a view showing the relationship between the position of the cuff 12 and the height of the heart.

In a case in which the subject places the blood pressure measurement device 2 on his or her own wrist, the subject puts on the blood pressure measurement device 2 while the forearm in front of the elbow is resting on a table, and the subject then raises the forearm so that the wrist on which the blood pressure measurement device 2 is worn is at the height h (mm) of the heart, but the height to which the wrist is moved in the vertical direction when the forearm is raised is measured by a pressure sensor. Air pressure is what can be detected directly by the pressure sensor, but the height from the table to the heart can be obtained from the air pressure on the table and the air pressure at the position of the heart.

Figure 3:
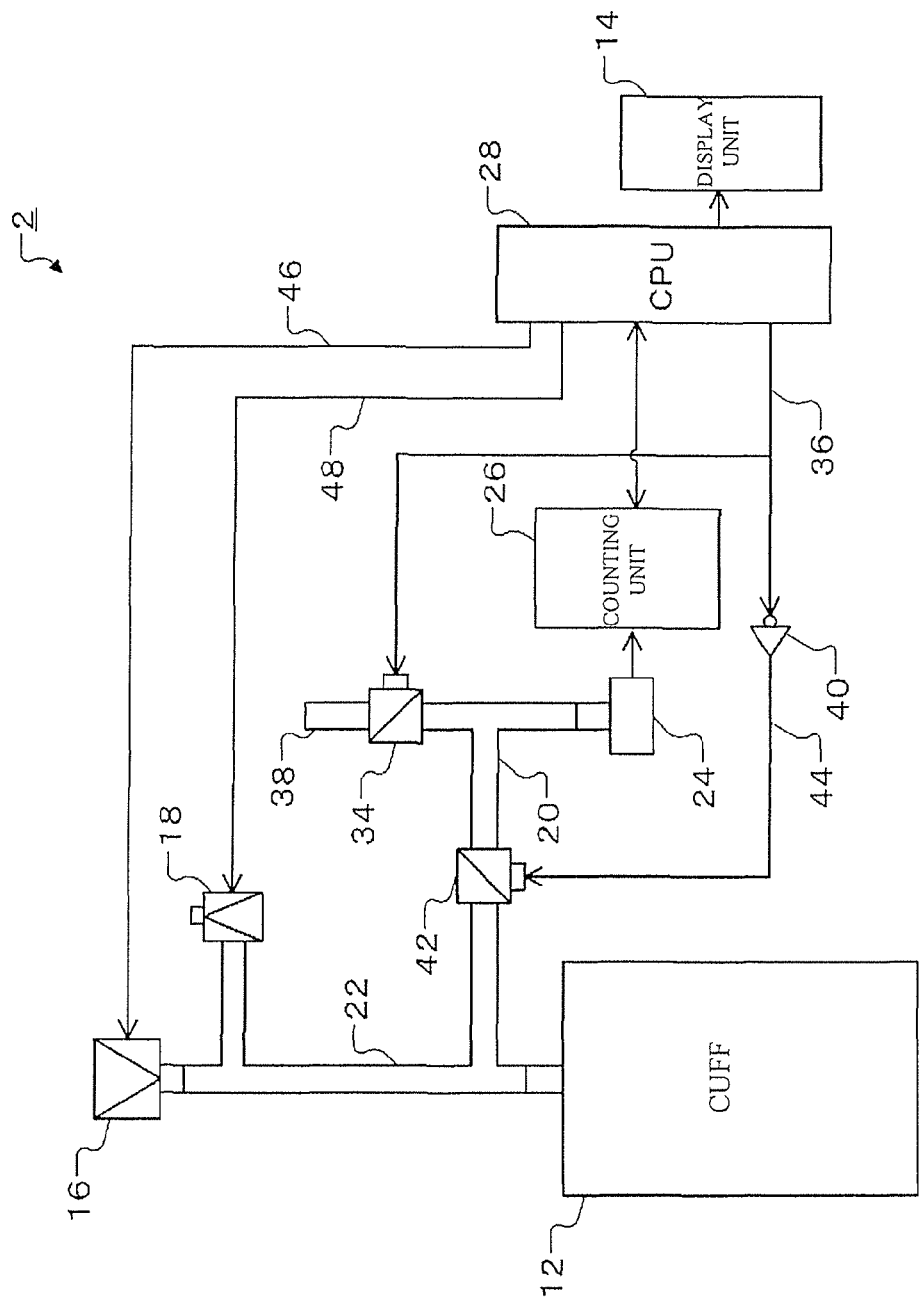
FIG. 3 is a block diagram showing the configuration of the electronic blood pressure gauge according to the present embodiment.

FIG. 3 is a block diagram showing the configuration of the blood pressure measurement device 2 according to the present embodiment.

In the blood pressure measurement device 2 according to the present embodiment, the body 10 is attached to the cuff 12 which is worn on the subject's wrist, and inside the body 10 are provided a pressurizing pump (pressurization unit) 16 for pressurizing the cuff 12; an air discharge unit 18 for discharging the air inside the cuff 12; pressure transmission channels 20, 22 for transmitting pressure; a pressure sensor (sensor) 24 for detecting the air pressure of the cuff 12 and the atmosphere; a counting unit 26 for counting a sensor signal of the pressure sensor 24; a CPU (control circuit) 28 for executing processing of a measurement switching unit, a blood pressure measurement unit, a blood pressure value correction unit, and other components for blood pressure measurement in accordance with a stored program; a storage unit 32 (see FIG. 4) for storing input data, computation data, measurement results, and other information; and a display unit 14 for displaying the measured blood pressure value.

The measurement switching unit switches between measurement of an internal pressure variation of the cuff 12 by the pressure sensor 24, and measurement of the atmospheric pressure at the position of the cuff 12 and the position of the heart of the subject wearing the cuff 12 by the pressure sensor 24. The blood pressure measurement unit acquires the sensor signal of the pressure sensor 24 from the measurement of the internal pressure variation of the cuff 12 by the pressure sensor 24, and computes a blood pressure value on the basis of the internal pressure variation of the cuff 12 as obtained from the sensor signal. The blood pressure value correction unit acquires the sensor signal of the pressure sensor 24 from the measurement of the atmospheric pressure at the position of the cuff 12 and at the position of the heart of the subject wearing the cuff 12 by the pressure sensor 24, and arithmetically applies to the blood pressure value computed by the blood pressure measurement unit a correction value that is in accordance with the difference in atmospheric pressure between the position of the cuff 12 and the position of the heart of the subject wearing the cuff 12 as obtained from the sensor signal. In the embodiment described above, the measurement switching unit, the blood pressure measurement unit, and the blood pressure value correction unit in the blood pressure measurement device 2 are realized by the CPU 28 processing a high-precision air pressure value from the counting unit 26 according to a predetermined program.

The blood pressure measurement device 2 according to the present embodiment is provided with a calibration mode, a blood pressure measurement mode, an altitude correction mode, and a re-measurement mode. Each mode is described below.

Calibration Mode

First, the height of the heart must be stored in the blood pressure measurement device 2 prior to measuring blood pressure. The CPU 28 executes the calibration mode in accordance with a setting by the subject or a condition set in advance. The CPU 28 at this time outputs a signal 36 for opening an electromagnetic valve 34, and the electromagnetic valve 34 opens to introduce atmospheric pressure to the pressure transmission channel 20 from an opening 38, at which time, the signal 36 is converted by a NOT circuit 40 into a signal 44 for closing an electromagnetic valve 42, the electromagnetic valve 42 closes, and the pressure transmission channel 22 from the cuff 12 is blocked. At the same time, the CPU 28 sets the counting unit 26 to the high-precision mode. A state thereby occurs in which atmospheric pressure is applied to the pressure sensor 24 via the pressure transmission channel 20, and the height position of the pressure sensor 24 (blood pressure measurement device 2) can be measured with high precision. The CPU 28 then instructs the subject to move the blood pressure measurement device 2 to the same height as the heart, and causes the current high-precision air pressure value to be stored in the storage unit 32 on the basis of a signal generated when the subject presses a pushbutton or the like of the operation input unit 30, for example.

Blood Pressure Measurement Mode

After height information for the heart has been stored by the calibration mode, the blood pressure measurement device 2 enters the blood pressure measurement mode. The CPU 28 outputs the signal 36 for closing the electromagnetic valve 34 and closes the electromagnetic valve 34, at which time the signal 36 is converted by the NOT circuit 40 into the signal 44 for opening the electromagnetic valve 42, and the electromagnetic valve 42 is opened. The pressure sensor 24 is thereby placed in the same pressure range as the cuff 12 via the pressure transmission channels 20, 22. At the same time, the CPU 28 changes the counting unit 26 to the blood pressure measurement mode, the pressure of the cuff 12 and minute pressure fluctuations thereof can then be measured, and the blood pressure measurement device 2 is prepared to function as a blood pressure gauge.

Subsequent operation is the same as that of normal blood pressure measurement. The CPU 28 outputs a drive signal 46, and after pressurization to a predetermined pressure by the pressurizing pump 16, a drive signal 48 is outputted to control the air discharge unit 18 so that the pressure of the cuff 12 is reduced by a certain percentage. Minute pressure fluctuations at this time are detected, and a tentative systolic blood pressure and diastolic blood pressure are computed in accordance with a specific algorithm. These operations are possible not only during depressurization, but also when the pressurizing pump 16 and the air discharge unit 18 are simultaneously controlled to increase the pressure of the cuff 12 by a certain ratio.

Altitude Correction Mode

After the tentative blood pressure values have been obtained, the CPU 28 returns to the same settings as the calibration mode and again measures the atmospheric pressure. The difference in altitude between the position of the heart and the height position of the pressure sensor 24 (blood pressure measurement device 2) during measurement can be computed by the following equation, for example, where $\Delta p$ (Pa) is the pressure difference between the heart calibration value previously stored in the storage unit 32 and the air pressure during measurement.

$$h(\text{mm}) = 0.023 / \Delta p$$

The true blood pressure is computed by using a conversion equation such as the one shown below, for example, from the altitude difference obtained above.

$$\text{True blood pressure} = \text{Measured value} + (h(\text{mm}) \times 1.055 / 13.6) \text{mmHg}$$

This true blood pressure value is displayed on the display unit 14, for example, to notify the subject, and measurement is ended. The current air pressure used for correction at this time is used for the next measurement as well, and is therefore stored in the storage unit 32.

Re-Measurement Mode

When the next blood pressure measurement begins, the current air pressure is measured in the same manner as the previous measurement, and the current air pressure is compared with the air pressure from the previous measurement stored in the storage unit 32. When the result of the comparison indicates no variation of more than a specified value, the CPU 28 continues to perform the same processing as in the blood pressure measurement mode described above, computes a blood pressure value, and displays the true blood pressure value on the display unit 14.

When the results of comparison show a divergence of more than a certain value, a posture change or fluctuation in atmospheric pressure is inferred, and the reference height calculated in the calibration mode cannot be used for water head correction. In this case, the CPU 28 displays an instruction to recalibrate on the display unit 14, and another blood pressure measurement is performed after the calibration mode is executed by the subject.

Figure 4:
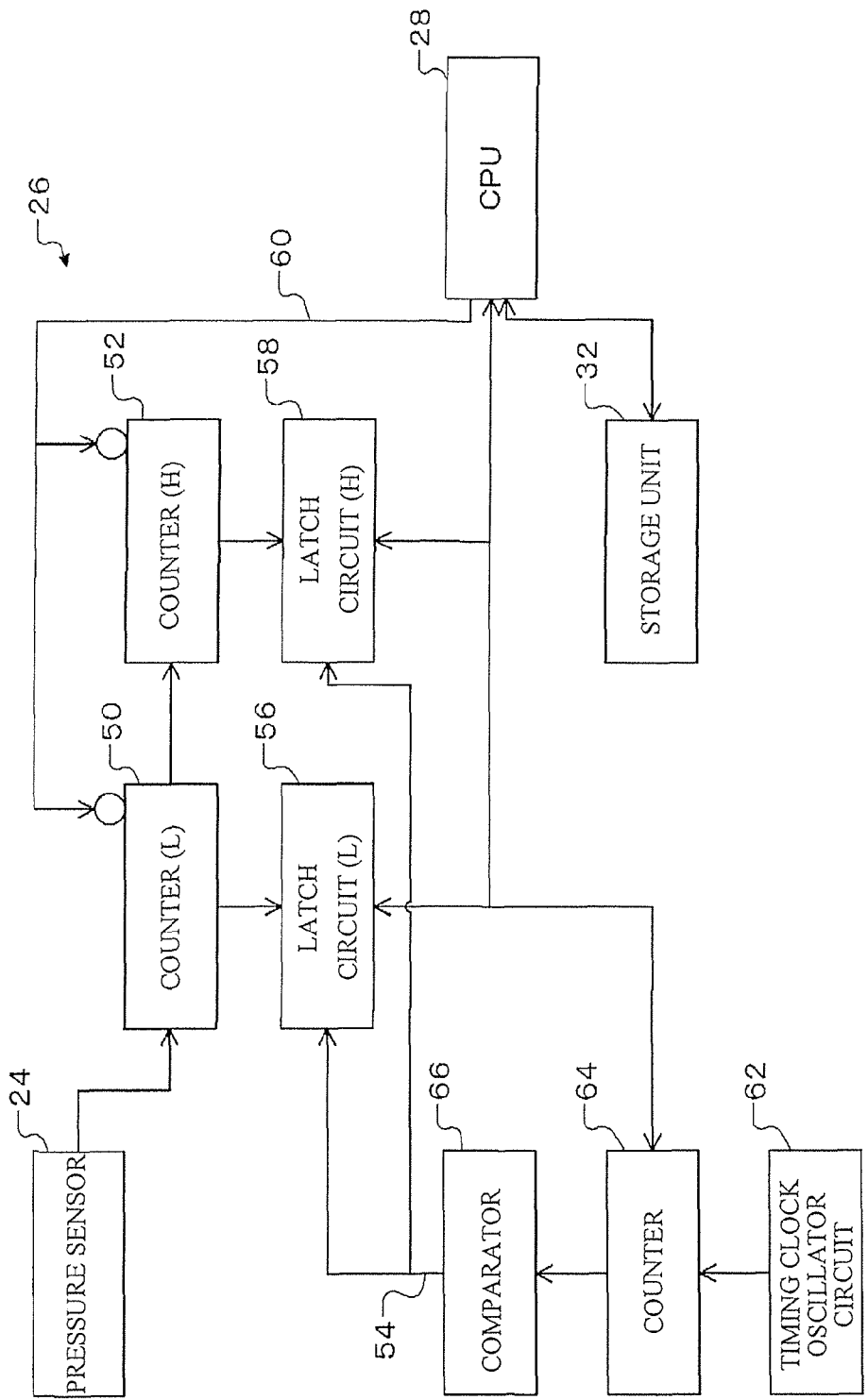
FIG. 4 is a block diagram showing the internal configuration of the counting unit shown in FIG. 3.

The actual operations of the calibration mode and the blood pressure measurement mode will be specifically described based on FIG. 4.

FIG. 4 is a block diagram showing the internal configuration of the counting unit 26 shown in FIG. 3.

The pressure sensor 24 is a sensor composed of a transducer which oscillates always at a certain characteristic frequency by application of a predetermined voltage, and an electronic circuit for electrically amplifying the oscillation waveform and outputting the oscillation waveform as a signal to the outside. When an atmospheric fluctuation or other pressure variation is applied to the transducer from the outside, the mechanical characteristics of the transducer change, and this change is detected from the outside as a change in the above-mentioned characteristic frequency. By measuring in this frequency and change thereof, the applied pressure change can be measured. This produces adequately high precision in comparison to a common pressure sensor, but even higher precision is necessary to detect the altitude change described above. The precision of a pressure sensor can be further enhanced by measuring the frequency over a certain period of time and calculating a time average. On the other hand, since no data are obtained for a certain period of time, temporal resolution is reduced, which can be considered a contradictory characteristic.

In order to measure a change in height as a change in air pressure, high precision on the order of (0.001 kPa) is needed, and a measurement time of approximately 50 ms (20 Hz) is needed to calculate a time average in order to achieve this precision.

In order to compute a blood pressure value, 10 Pa units of pressure represent adequate precision, but since blood pressure information is obtained from the shape of the pulse waveform, the temporal resolution must be 100 Hz (10 msec) or higher, and these conditions cannot both be satisfied given the requirements described above.

In the present embodiment, the pulse signal from the pressure sensor 24 is counted by a counter (L) 50 and a counter (H) 52, stored by a latch circuit (L) 56 and a latch circuit (H) 58 by a latch signal 54 at a predetermined timing, and read from the CPU 28, as shown in FIG. 4.

A count value obtained at predetermined time intervals is determined in advance from the characteristics of the pressure sensor 24, and the CPU 28 computes the average pressure within a predetermined time period on the basis of a pressure-frequency conversion table maintained in the program.

The CPU 28 then outputs a reset signal 60 and returns the values of the counter (L) 50 and counter (H) 52 to zero. A signal from a timing clock oscillator circuit 62 is counted by a counter 64, and the latch signal 54 is generated each time the signal of the timing clock oscillator circuit 62 is equal to a value set in a comparator 66. Specifically, the latch signal 54 is generated at a pre-set time interval. The CPU 28 repeats this series of operations, thereby enabling a continuous pressure signal to be obtained.

In the calibration mode (high-precision), the CPU 28 sets a value corresponding to 50 msec in the comparator 66. In the blood pressure measurement mode, the CPU 28 sets a value corresponding to 10 msec or a smaller desired time interval in the comparator 66. The pressure measurement precision and temporal resolution can thus be freely switched, and the necessary functions can be provided by a single pressure sensor. The pressure sensor thereby has adequate pressure precision to detect an altitude difference by the water head value and to estimate a blood pressure value.

Figure 5:
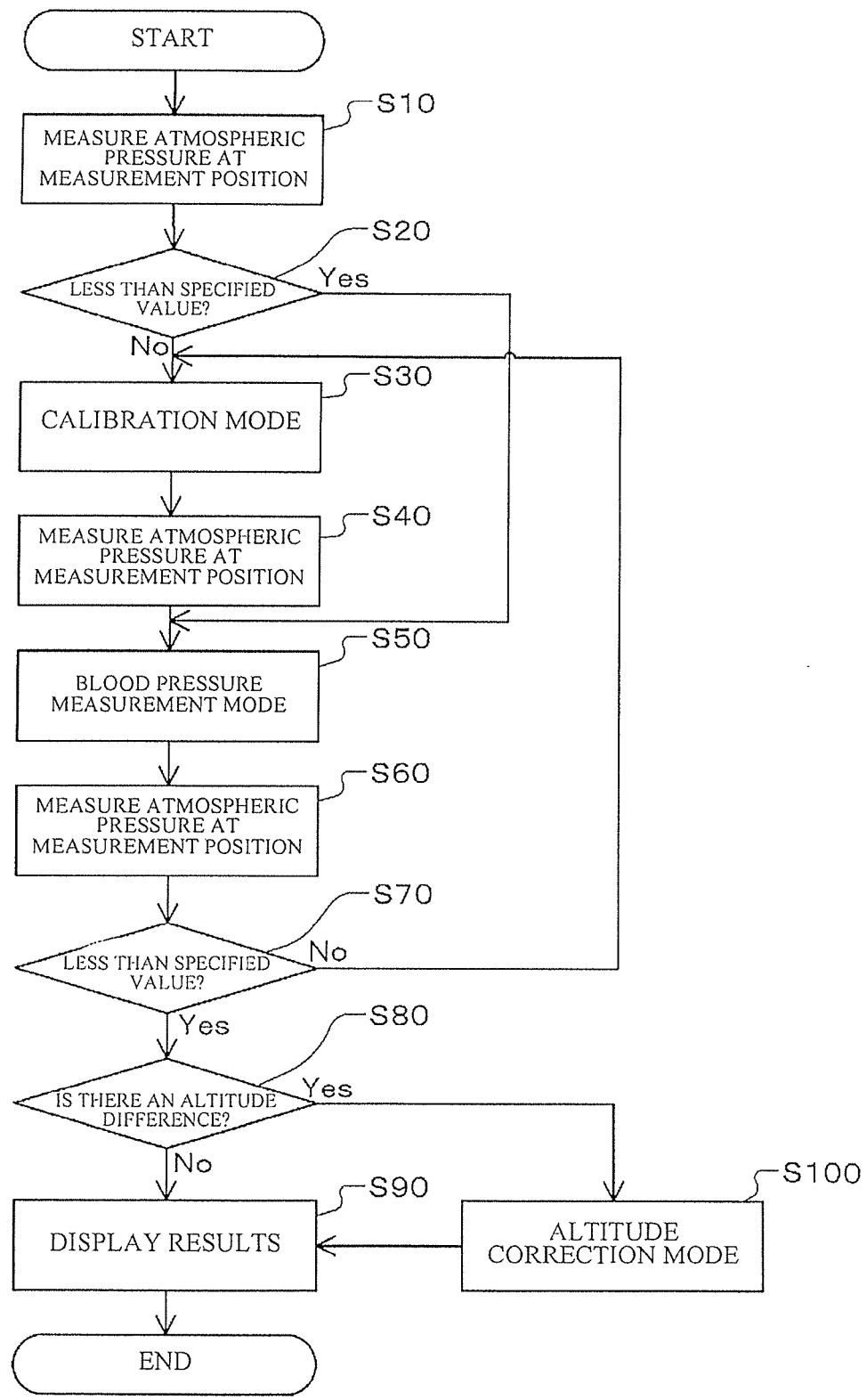
FIG. 5 is a flowchart showing the specifics of processing by the relevant parts of the control function of the electronic blood pressure gauge according to the present embodiment.

FIG. 5 is a flowchart showing the specifics of processing by the relevant parts of the control function of the blood pressure measurement device 2 according to the present embodiment. The process shown in this flowchart is begun by pressing a measurement start button of the operation input unit 30.

When the power is turned on and operation started in the blood pressure measurement device 2 according to the present embodiment, a zero setting, i.e., an initial reset, is completed.

First, in step S10, the CPU 28 outputs the signal 36 for opening the electromagnetic valve 34, and the electromagnetic valve 34 opens to introduce atmospheric pressure to the pressure transmission channel 20 from the opening 38, at which time, the signal 36 is converted by the NOT circuit 40 into the signal 44 for closing the electromagnetic valve 42, the electromagnetic valve 42 closes, and the pressure transmission channel 22 from the cuff 12 is blocked. At the same time, the CPU 28 sets the counting unit 26 to the high-precision mode. A state thereby occurs in which atmospheric pressure is applied to the pressure sensor 24 via the pressure transmission channel 20, and the height position of the pressure sensor 24 (blood pressure measurement device 2) can be measured with high precision. A measurement position atmospheric pressure value A which is the high-precision air pressure value at that time is stored in the storage unit 32 on the basis of the signal of a pushbutton or the like of the operation input unit 30 pushed by the subject, for example. The stored value serves as height data for the measurement position.

Then, in step S20, the CPU 28 determines the pressure difference Δp (Pa) between the measurement position atmospheric pressure value C (the initial value of which is a predetermined value) stored in the storage unit 32 during the previous blood pressure measurement and the measurement position atmospheric pressure value A of the current measurement, expressed in units of blood pressure, in the same manner as in the altitude correction mode described above. For example, in a case in which the specified value is 5 mmHg, when the difference is less than 5 mmHg (step S20: Yes), the process proceeds to step S50. When the difference is greater than 5 mmHg (step S20: No), the process proceeds to step S30.

Then, in step S30, the CPU 28 through the use of the display unit 14 or another component instructs the subject to move the blood pressure measurement device 2 to the same height as the heart, and causes a heart position atmospheric pressure value B which is the current high-precision air pressure value to be stored in the storage unit 32 on the basis of a signal generated when the subject presses a pushbutton or the like of the operation input unit 30, for example. The stored value serves as height data for the position of the heart.

Then, in step S40, the CPU 28 through the use of the display unit 14 or another component instructs the subject to move the blood pressure measurement device 2 to the measurement position, and causes the measurement position atmospheric pressure value A which is the current high-precision air pressure value to be stored in the storage unit 32 on the basis of a signal generated when the subject presses a pushbutton or the like of the operation input unit 30, for example. The stored value serves as height data for the measurement position prior to blood pressure measurement.

Then, in step S50, the CPU 28 outputs the signal 36 for closing the electromagnetic valve 34 and closes the electromagnetic valve 34, at which time the signal 36 is converted by the NOT circuit 40 into the signal 44 for opening the electromagnetic valve 42, and the electromagnetic valve 42 is opened. The pressure sensor 24 is thereby placed in the same pressure range as the cuff 12 via the pressure transmission channels 20, 22. At the same time, the CPU 28 changes the counting unit 26 to the blood pressure measurement mode, the pressure of the cuff 12 and minute pressure fluctuations thereof can then be measured, and the blood pressure measurement device 2 is prepared to function as a blood pressure gauge.

Subsequent operation is the same as that of normal blood pressure measurement. The CPU 28 outputs a drive signal 46, and after pressurization to a predetermined pressure by the pressurizing pump 16, a drive signal 48 is outputted to control the air discharge unit 18 so that the pressure of the cuff 12 is reduced by a certain percentage. Minute pressure fluctuations at this time are detected, and a tentative systolic blood pressure and diastolic blood pressure are computed in accordance with a specific algorithm. These operations are possible not only during depressurization, but also when the pressurizing pump 16 and the air discharge unit 18 are simultaneously controlled to increase the pressure of the cuff 12 by a certain ratio.

In the next step S60, after the tentative blood pressure values have been obtained, the CPU 28 returns to the same settings as in step S40 and again measures the atmospheric pressure. The measurement position atmospheric pressure value C which is the current high-precision air pressure value is stored in the storage unit 32 on the basis of a signal generated when the subject presses a pushbutton or the like of the operation input unit 30, for example. The stored value serves as height data for the measurement position after blood pressure measurement.

Then, in step S70, the CPU 28 determines the pressure difference Δp (Pa) between the measurement position atmospheric pressure value A stored in step S40 and the measurement position atmospheric pressure value C stored in step S60, expressed in units of blood pressure, in the same manner as in the altitude correction mode described above. For example, in a case in which the specified value is 5 mmHg, when the difference is less than 5 mmHg (step S70: Yes), the process proceeds to step S80. When the difference is greater than 5 mmHg (step S70: No), the process returns to step S30, and the atmospheric pressure at the heart position is measured.

In the next step S80, the CPU 28 determines the pressure difference Δp (Pa) between the heart position atmospheric pressure value B stored in step S30 and the measurement position atmospheric pressure value C stored in step S60, expressed in units of blood pressure, in the same manner as in the altitude correction mode described above. For example, in a case in which the specified value is 5 mmHg, when the difference is less than 5 mmHg (step S80: No), the process proceeds to step S90. When the difference is greater than 5 mmHg (step S80: Yes), the process proceeds to step S100.

Then, in step S90, the CPU 28 displays the pre-correction and post-correction blood pressure values on the display unit 14 as the results of blood pressure measurement, notifies the subject, and ends blood pressure measurement.

In the next step S100, the CPU 28 computes a corresponding pressure correction value from the computed pressure difference due to height of the heart and cuff 12. The blood pressure measurement (determination) results are then corrected. The blood pressure values are corrected by applying an arithmetic correction to the determined blood pressure values on the basis of the pressure correction value. When the pressure difference between the heart position atmospheric pressure value B stored in step S30 and the measurement position atmospheric pressure value C stored in step S60 is expressed as Δp (Pa), the difference in altitude between the heart position and the measurement position can be computed by the equation for the altitude correction mode described above. The current air pressure value used for the correction at this time is used in the next measurement as well, and is therefore stored in the storage unit 32.

In the present embodiment, by alternately measuring blood pressure and air pressure, the values obtained can also be used to determine whether the arm has moved, i.e., whether the measured value is correct, during blood pressure measurement.

The entire disclosure of Japanese Patent Application No. 2009-261583, filed Nov. 17, 2009 is expressly incorporated by reference herein.

What is claimed is:

1. A blood pressure measurement device to measure blood pressure of a subject, the blood pressure measurement device comprising:
    a blood pressure transmitting part;
    a pressure transmission channel configured to be selectively switched between an air pressure state in which atmospheric pressure is introduced to the pressure transmission channel and an internal pressure state in which an internal pressure of the blood pressure transmitting part is introduced to the pressure transmission channel;
    a sensor coupled to the pressure transmission channel to measure air pressure in the pressure transmission channel in the air pressure state at first and second positions and to measure an internal pressure variation in the pressure transmission channel in the internal pressure state at the second position;
    a counting unit configured to count a sensor signal of the sensor with a first frequency in the air pressure state, and to count the sensor signal of the sensor with a second frequency in the internal pressure state, the second frequency being higher than the first frequency;
    an instruction component configured to instruct the subject to move the blood pressure transmitting part to the first position adjacent to a heart of the subject, in order to measure the air pressure by the sensor at the first position;
    a measurement switching unit configured to switch a pressure state for measurement between the internal pressure state and the air pressure state;
    a blood pressure measuring part configured to compute a blood pressure value on the basis of the internal pressure variation obtained from the sensor signal counted in the counting unit; and
    a blood pressure value correction unit configured to arithmetically apply to the computed blood pressure value a correction value that is in accordance with the difference in the air pressure between the second position and the first position as obtained from the sensor signal of the sensor counted in the counting unit.

2. The blood pressure measurement device according to claim 1, wherein
    a precision of measuring the air pressure at the second position and the first position through the use of the sensor in the air pressure state is more precise than a precision of measuring the internal pressure variation through the use of the sensor in the internal pressure state.

3. A blood pressure measurement device to measure blood pressure of a subject, the blood pressure measurement device comprising:
    a sensor configured to measure air pressure at first and second positions while a state for measurement is in an air pressure state in which atmospheric pressure is measured by the sensor, and to measure an internal pressure variation at the second position while a state for measurement is in an internal pressure state in which an internal pressure of a blood pressure transmitting part is measured by the sensor;

a counting unit configured to count a sensor signal of the sensor with a first frequency in the air pressure state, and to count the sensor signal of the sensor with a second frequency in the internal pressure state, the second frequency being higher than the first frequency; and a blood pressure measuring part configured to measure the blood pressure based on the internal pressure variation at the second position in accordance with the difference between the air pressure at the first position and the air pressure at the second position obtained by the sensor signal counted in the counting unit.

4. The blood pressure measurement device according to claim 3, further comprising a measurement switching unit configured to switch between measurement of the internal pressure variation by the sensor at the second position, and measurement of the air pressure at the first position and at the second position by the sensor.

5. The blood pressure measurement device according to claim 4, further comprising an instruction component configured to instruct the subject to move the sensor to the first position from the second position.

6. A blood pressure measurement device to measure blood pressure of a subject, the blood pressure measurement device comprising:

a blood pressure transmitting part;

a pressure transmission channel configured to be selectively switched between an air pressure state in which atmospheric pressure is introduced to the pressure transmission channel and an internal pressure state in which an internal pressure of the blood pressure transmitting part is introduced to the pressure transmission channel;

a sensor configured to measure air pressure in the air pressure state and to measure blood pressure of a subject in the internal pressure state;

a counting unit configured to count a sensor signal of the sensor with a first frequency in the air pressure state, and to count the sensor signal of the sensor with a second frequency in the internal pressure state, the second frequency being higher than the first frequency;

a blood pressure measuring part configured to compute a blood pressure value on the basis of the internal pressure variation of the blood pressure transmitting part obtained from the sensor signal counted in the counting unit in the internal pressure state, and to measure the air pressure based on the sensor signal counted in the counting unit in the air pressure state, and arithmetically apply to the computed blood pressure value a correction value on the basis of an air pressure variation.

7. The blood pressure measurement device according to claim 6, further comprising a measurement switching unit configured to switch a pressure state for measurement between an internal pressure state for measurement of the internal pressure variation by the sensor at the second position, and an air pressure state for measurement of the air pressure by the sensor at the second position and the first position.

* * * * *